United States Patent [19]

Lane et al.

[11] 4,273,678

[45] Jun. 16, 1981

[54] METHOD OF PREPARING AN OXYCHLORINATION CATALYST

[75] Inventors: Ruth M. Lane; Martyn H. Stacey, both of Runcorn, England

[73] Assignee: Imperial Chemical Industries Limited, London, England

[21] Appl. No.: 38,076

[22] Filed: May 11, 1979

Related U.S. Application Data

[60] Division of Ser. No. 878,473, Feb. 16, 1978, abandoned, which is a continuation of Ser. No. 431,323, Dec. 28, 1973, abandoned.

[30] Foreign Application Priority Data

Jan. 9, 1973 [GB] United Kingdom ............... 1118/73

[51] Int. Cl.$^3$ ................... B01J 21/04; B01J 21/10; B01J 23/72
[52] U.S. Cl. ................................ 252/463; 570/243
[58] Field of Search ............... 252/463; 260/654 A, 260/655, 656 R, 658 R, 659 A, 662 A

[56] References Cited

U.S. PATENT DOCUMENTS

| | | | |
|---|---|---|---|
| 2,327,174 | 8/1943 | Cass | 260/659 A |
| 2,379,414 | 7/1945 | Cass | 260/662 A |
| 3,374,183 | 3/1968 | Cooper | 252/463 |
| 3,454,663 | 7/1969 | Ryckaert et al. | 260/659 A |
| 3,461,084 | 8/1969 | Li | 260/659 A |
| 3,624,170 | 11/1971 | Wakiyama et al. | 260/659 A |

FOREIGN PATENT DOCUMENTS

167846 11/1953 Australia ............... 260/659 A
971996 10/1964 United Kingdom .

*Primary Examiner*—W. J. Shine
*Attorney, Agent, or Firm*—Cushman, Darby & Cushman

[57] ABSTRACT

An oxychlorination catalyst which is an intimate mixture of the oxides of magnesium, aluminum and copper obtained by calcining is prepared by precipitating the hydrated oxides of magnesium and aluminum, drying and calcining these hydrated oxides to form a mixed oxide of magnesium and aluminum, treating the mixed oxide with a copper salt solution and again calcining to provide the copper oxide.

6 Claims, No Drawings

METHOD OF PREPARING AN OXYCHLORINATION CATALYST

This is a division of application Ser. No. 878,473 filed Feb. 16, 1978, abandoned which is a continuation of application Ser. No. 431,323, filed Dec. 28, 1973, now abandoned.

This invention relates to catalytic oxyhalogenation processes and catalysts therefor.

It is known to use copper compounds as catalysts in oxyhalogenation reactions and it is known that copper compounds can be used in admixture with other compounds or carried upon a support material, for example alumina, to improve their catalytic efficiency.

We have now found that improved results can be obtained in oxyhalogenation processes by using as catalyst a material containing the oxides of magnesium, aluminium and copper.

Thus according to the present invention we provide a process for the catalytic oxyhalogenation of a hydrocarbon or halogenated hydrocarbon feedstock which comprises carrying out the oxyhalogenation reaction in the presence of a catalyst which is an intimate mixture of the oxides of magnesium, aluminium and copper.

The feedstock used may be saturated or unsaturated in nature, and may comprise for example a hydrocarbon of 1 to 4 carbon atoms or a halogenated derivative (for example a fluorinated or chlorofluorinated derivative but especially a chlorinated derivative) thereof. If desired the feedstock may comprise mixtures of two or more such compounds. Examples of feedstocks which may conveniently be used include ethylene, ethane, propane, propylene, butane, chloroethanes (monochloro or polychloro), chloroethylenes and mixtures thereof. Commercially-available mixtures, for example ethane/ethylene mixtures and the mixed chlorinated hydrocarbons available from other processes may be used if desired.

The catalysts to be used in the present process have characteristics which render them eminently suitable for use in oxychlorination reactions and their preparation is based in part on precipitation and/or calcination techniques.

The copper oxide component must be brought into intimate mixture with the other component oxides. This can be done by forming the copper oxide from a precursor in the presence of the other two oxides. A very convenient precursor, for each of the three metals, is the hydroxide (hydrated oxide) as this is readily converted by heat treatment into the corresponding metal oxide. Other precursors may be used if desired, however, for example heat-decomposable salts and especially one or more nitrates.

The desired intimate mixture of metal oxides can be obtained by heating the mixed hydroxides of the three metals, and these hydroxides can be prepared individually and then mixed in the desired proportions or may be prepared by co-precipitation. Such co-precipitation can be carried out substantially simultaneously by precipitation from a solution containing a mixture of all the three metals (copper, magnesium and aluminium), but is preferably carried out sequentially. When a sequential precipitation is employed, it is preferred that the copper component should be incorporated last. If desired, two of the metals may be obtained as a mixture of their oxides by decomposition of their mixed precursors (for example by heating their co-precipitated hydroxides) and this mixture of two oxides can then be treated so as to incorporate the third metal oxide intimately, for example by impregnation with the precursor or precipitation of the precursor upon it, followed by a heat treatment which completes the conversion to the desired mixture of three oxides.

It is especially preferred to make the catalyst by treating a mixed magnesium oxide/aluminium oxide with a soluble copper salt and then heating the resulting mixture to convert the copper component to oxide.

The mixed magnesium oxide/aluminium oxide may be made in a variety of ways, of which the following are examples:

1. A solution (conveniently an aqueous solution) of salts of magnesium and aluminium is prepared and the metals are co-precipitated from this in the form of their hydrated oxides. The precipitation can be carried out at ambient temperature (about 20° C.) and at a pH greater than 8.0 (for example at pH 9.3). The precipitate is collected, dried and calcined.

2. A solution of alkoxides of magnesium and aluminium (for example the ethoxides) is hydrolysed by treatment with water. This can be done in cooled ethanol solution, by addition of an ethanol/water mixture. The mixture can be diluted as necessary with water and the mixed hydroxides collected by filtration, dried and calcined.

3. A solution of a magnesium salt is mixed with a solution of an alkali metal aluminate (for example sodium aluminate) and the resulting precipitate is collected by filtration, washed, dried and calcined. The solutions are conveniently aqueous solutions, and the pH of the separate mixtures and/or their mixture may be adjusted as necessary (for example by addition of acid or base) to achieve substantially complete co-precipitation.

4. A mixture of soluble precursors (for example magnesium and aluminium nitrates) is obtained by drying a mixed solution (for example by freeze-drying or spray-drying techniques) and calcining the mixture to form the oxides.

5. Alumina of convenient particle size (for example a microspheroidal alumina of desired fluidisable characteristics) is mixed with a solution of a thermally decomposable magnesium salt (for example magnesium nitrate), and the mixture is dried and calcined.

The mixture of magnesium and aluminium oxides may contain an excess of one or other. For example, there may be used mixed oxides in which the proportion of magnesium oxide (MgO) is in the range 0.25 to 2.0 moles per mole of aluminium oxide ($Al_2O_3$). Generally, we find that the surface area of the mixed oxide decreases as the proportion of magnesium oxide increases. An intimate mixture containing the two oxides in the proportion of 0.9 to 1.1 moles of magnesium oxide per mole of aluminium oxide ($Al_2O_3$) is especially convenient; if desired, this ratio can be alternatively described as an atomic ratio of 0.9 to 1.1 atomic proportions of magnesium per two atomic proportions of aluminium.

For incorporation of the copper component, the mixed magnesium oxide/aluminium oxide may most conveniently be converted first to an aqueous slurry or suspension, and then mixing this with an aqueous solution of a copper salt (conveniently a cupric salt). The copper may be precipitated on the mixed oxide by addition of a base but usually precipitation occurs readily with some of the magnesium going into solution to displace the copper from solution. The resulting solid may then be collected by filtration, washed, dried and calcined.

The precipitating agent for the metals may be a base, for example an alkali metal hydroxide or carbonate, conveniently in aqueous solution. When using an alkali metal compound as precipitant it is usually preferred to wash the precipitate thoroughly to remove alkali metal ions before drying and calcination. It is preferred to use as precipitant a base which is volatile or which forms compounds readily lost in the calcination, for example ammonia or aqueous solutions thereof (ammonium hydroxide), as this reduces the need for thorough washing.

In the calcination treatment to produce the mixed oxides of magnesium and aluminium the temperatures preferably should not exceed 700° C. nor be less than 300° C. Below 300° C. no spinel is formed. As the temperature is increased from 300° C. to 700° C. an increasing percentage of spinel is formed. The calcination temperature should not exceed 700° C. as at this temperature and upwards too high a percentage of the spinel is formed and this is not particularly useful in the oxychlorination process of the present invention. Mixtures of aluminium oxide and magnesium oxide having a degree of spinel structure not more than 40% are preferred in the present process to those having a higher degree of spinel structure. The most preferred degree of spinel is not more than 25%. Such materials may be obtained when using calcination temperature in the preferred range of 350° C. to 600° C.

Similar temperatures may be used for heating the mixed magnesium, aluminium and copper oxides, and similar preferences apply.

When the catalyst is made from a mixed magnesium oxide/aluminium oxide which already has a spinel structure, either partly or completely, we believe that the treatment of this with a copper salt causes copper ions to enter into the lattice structure of the spinel and the equivalent amount of magnesium goes into solution. Whether this is so is not certain, but the copper component apears to be very strongly held; this is shown by the fact that, when the copper-containing catalyst is washed with water and dilute hydrochloric acid, soluble copper salts are not readily formed or found in the washings.

When the mixed oxides containing the copper component are calcined at the temperatures used in making the magnesium oxide/aluminium oxide mixture, such spinel structure as already existed in the binary oxide mixture remains and some migration of the copper into the spinel structure may occur. If the copper-containing catalyst mixture is heated to higher temperatures, however, some increase in spinel content may occur. Heating of the mixture of oxides in a form which contains little or no spinel structure will produce some degree of spinel formation according to the time and temperature employed.

Similarly, the surface area (as measured by the standard nitrogen absorption technique) of the mixed oxides are almost identical, regardless of whether they contain magnesium and aluminium oxides only or contain copper also, when calcined at a given temperature.

For the purpose of the present invention all measurements of percentage spinel in the catalysts referred to in this specification are determined by the X-ray diffraction method now described below. The values quoted are all relative to this method and are not intended to be absolute.

A sample of the material to be tested is first ground to pass a 300 mesh sieve (British Standard Specification). Ten parts by weight of the ground sample are thoroughly mixed with one part by weight or pure crystalline silicon powder which has also been ground to pass through a sieve of the same size. A portion of this mixture is mounted in the rotating sample holder of a Philips PW1050 X-ray diffractometer. The X-ray diffraction pattern of the sample is obtained using a copper target X-ray tube and a proportional counter detector fitted with a nickel filter, 0.02 mm thick.

The silicon 111 peak is measured by scanning over the range $27.24°2\theta$ to $29.24°2\theta$ and the spinel 220 peak is measured by scanning over the range of $29.24°2\theta$ to $33.24°2\theta$. In each case the net peak area is obtained by subtracting the background obtained by drawing a straight line between the two minima on either side of the peak within the respective angular range from the integrated area between these minima.

The ratio of the net spinel peak area to the net silicon peak area is obtained as follows:

$$\text{Ratio (sample)} = \frac{\text{Net Peak Area of Spinel 220 Peak of Sample}}{\text{Net Peak Area of Silicon 111 Peak}}$$

A similar measurement is then made using a standard spinel sample in place of the material to be tested and a second ratio is obtained for the standard as follows:

$$\text{Ratio (standard)} = \frac{\text{Net Peak Area of Spinel 220 Peak of Standard}}{\text{Net Peak Area of Silicon 111 Peak}}$$

From these two ratios the percentage spinel in the material to be tested is obtained from the relation:

$$\text{Percentage Spinel in Sample} = \frac{\text{Ratio (sample)}}{\text{Ratio (standard)}} \times 100\%$$

The standard spinel of chemical formula $MgAl_2O_4$ for comparison with the material to be tested is prepared in the following manner. An aqueous solution containing magnesium nitrate and aluminium nitrate in a molar ratio of 1:2 at a concentration of approximately 0.75 molar total, is mixed with ammonia solution at a concentration of approximately 2.0 molar by running both into a reaction vessel in such a way as to maintain the pH of the resulting mixture at approximately 9.5. The mixture is heated to 70° C. for 2 hours. The precipitate produced is separated by filtration, dried at 100° C., calcined at 1000° C. for 6 hours and finally calcined at 1200° C. for a further 24 hours. Material prepared according to this method was found to give a diffraction peak area ratio, Ratio (standard) as defined above of 130.

As the magnesium oxide content of the present catalyst is increased at constant copper content burning of ethylene to carbon oxides is reduced. Also the effect of increasing the magnesium oxide content is to increase the temperature at which hydrogen chloride conversion is a maximum and the effect is greater the greater the copper oxide content. Increased magnesium oxide content leads in the oxychlorination of ethylene to an increase in selectivity to 1,2-dichloroethane.

In the present catalyst the proportion of copper may be such as to provide 1 to 50, for example, 4 to 30 atomic proportions of copper per 100 atomic proportions of magnesium. Surprisingly small proportions of copper in the present catalysts are found to be very effective in oxychlorination reactions. Thus useful results can be obtained when there is present 3 to 15 atomic proportions of copper for each 100 atomic proportions of magnesium. The latter amounts to on only 1.25% to 6.4% by weight copper in a catalyst in which there is substantially one atomic proportion of magnesium per two atomic proportions of aluminium.

By varying the copper content of the catalyst at constant magnesium oxide content the temperature at which hydrogen chloride conversion is an optimum can be altered. There is no substantial loss in hydrogen chloride conversion by using low copper contents as this is compensated for by the higher operating optimum temperature.

In the oxychlorination reaction there is slight pick up of chloride ion by the catalyst but the present catalyst remains essentially as an intimate mixture of copper oxide, magnesium oxide and aluminium oxide. The catalysts are poorly crystalline in structure and contain some crystallites of small size usually in the range 10 Å to 1000 Å. Generally the surface area of the catalysts is in the range 80 m$^2$/g to 150 m$^2$/g, they have a pore volume (as measured by nitrogen adsorption, helium/air pyknometry and mercury porosimetry techniques) of 0.3 to 0.6 and are eminently suitable for oxychlorination reactions in a fluidised bed.

The oxyhalogenation process may be carried out under the conditions conventionally employed for such processes, although higher temperature conditions than conventional may be used in the present process. The present process may for example be carried out for the oxychlorination of ethylene at temperatures in the range 200° C. to 350° C., and at any convenient pressure. The halogen may especially be chlorine though it may be another, for example bromine. The source of chlorine may be hydrogen chloride or chlorine. The oxygen necessary for the oxyhalogenation reaction may be provided in any convenient or conventional form, for example as oxygen itself or as an oxygen-containing gas, for example air.

The present catalysts can be used at high temperatures, they can give high space time yields, good conversions on chlorine, high selectivities to 1,2-dichloroethane, there is little loss of copper by volatilisation, there is low burning of the organic reactant, they are not liable to sticking and are of good chemical stability.

The invention is illustrated but not limited by the following Examples in which the parts and percentages are by weight unless otherwise stated.

EXAMPLE 1

An intimate mixture of the hydroxides of magnesium and aluminium was prepared by co-precipitation with ammonia at ambient temperature at pH 9.5 from an aqueous solution of magnesium and aluminium nitrates in the molar ratio 1:2. The precipitate was filtered off, washed, dried at 120° C. and calcined for 48 hours at temperatures described hereinafter. The mixed oxides were placed in a vessel containing 30 parts of water and 30 parts of aqueous N/10 nitric acid and the mixture was stirred vigorously. 7 parts of an aqueous solution containing 0.17 parts cupric nitrate trihydrate were slowly added to the mixture, which was stirred at ambient temperature for 4 hours. The resulting pale blue solid was then collected by filtration and washed with water. Analysis of the aqueous filtrate showed that it contained a negligible amount of copper and aluminium but approximately 4% of the original amount of magnesium was present in it. The precipitate was dried at 120° C. for 4 hours and then calcined in air at temperatures also described hereinafter for 6 hours. Analyses of the catalyst showed them to contain 4.16 gram atoms of copper per 100 gram atoms of magnesium and approximately 1 gram atom of magnesium per 2 gram atoms of aluminium.

Catalysts containing different percentages of spinel as obtained by calcination at different temperatures were thus prepared.

Specimens (0.2 g) of the catalysts of 60 to 100 mesh (British Standard Sieve) were placed as a fixed bed in a quartz tube which was surrounded by a block furnace. The catalysts were purged by treatment overnight at 300° C. with a stream of nitrogen. A stream consisting of $C_2H_4/O_2/HCl/N_2$ in the ratio (by volume) of 1:1:2:6 was passed through the reaction tube at 300° C. with a contact time of 0.5 sec to 0.75 sec. The inlet and exit gases were analysed chromatographically. The conditions of the runs and the results obtained are shown in Table I. In this and the following Examples EDC means 1,2-dichloroethane. VC means vinyl chloride, EC means ethyl chloride. The surface area of the copper-containing catalysts of Runs 1, 2 and 3 were (m$^2$/g) 145, 95 and 40 respectively.

TABLE 1

| Run No. | Calcination temp. of oxides of Mg and Al (°C.) | Calcination temperature of catalyst containing oxides of Mg/Al/Cu | Spinel content as herein before defined % | Selectivity of Product Formation % v/v | | | |
|---|---|---|---|---|---|---|---|
| | | | | EDC | VC | Other chlorinated $C_2-C_1$ hydrocarbons | $CO + CO_2$ |
| 1 | 400 | 400 | 5 | 94.9 | 0.6 | 1.6 | 2.9 |
| 2 | 600 | 600 | 18 | 97.0 | 0.5 | 2.5 | — |
| 3 | 600 | 1050 | 70 | 83.9 | 0.6 | 15.5 | — |

It was apparent that at the calcination temperature of 400° C. to 600° C. the selectivity for EDC formation is high but at calcination temperatures above 600° C. the purity of the EDC product drops markedly.

EXAMPLE 2

Catalysts of different copper contents but of approximately the same spinel content (about 18%) were prepared in a similar manner to that described in Example 1 and were tested in the oxychlorination of ethylene. The conditions under which they were used and the results obtained are shown in Table II.

TABLE II

| Catalyst (molar proportions) | Calcination temp °C. of MgO . Al$_2$O$_3$ | Calcination temp °C. of copper-containing catalyst | Reaction temp. °C. | Selectivity of Product Formation | | | | |
|---|---|---|---|---|---|---|---|---|
| | | | | EDC | VC | EC | other chlorinated C$_2$-C$_1$ hydrocarbons | CO + CO$_2$ |
| 0.02 CuO, 0.98 MgO, 1.00 Al$_2$O$_3$ (0.9% Cu) | 600 | 600 | 350 | 86 | 4.6 | 5.9 | 0.7 | 2.8 |
| 0.04 CuO, 0.96 MgO, 1.00 Al$_2$O$_3$ (1.8% Cu) | 600 | 600 | 300 | 97 | 0.5 | 2.5 | — | — |
| | | | 350 | 93.1 | 1.4 | 0.6 | 2.9 | 2.0 |
| 0.20 CuO, 0.85 MgO, 1.00 Al$_2$O$_3$ (8.4% Cu) | 600 | 400 | 250 | 97.3 | 0.4 | 0.5 | 0.1 | 1.7 |
| | | | 300 | 91.7 | 1.0 | 0.2 | 0.6 | 6.5 |

Comparison

By way of comparison runs were carried out under similar conditions as for Example 2 but with conventional catalysts consisting of (a) Cupric chloride supported on alumina (6.5% Cu), (b) a catalyst consisting of copper and aluminium oxides (approximate composition 0.1 CuO, 1.00 Al$_2$O$_3$) prepared by coprecipitation from their salts followed by repeated washing of the precipitate with water, drying and calcining at 400° C.; this catalyst contained 5.8% Cu (c) a mixture of magnesium and aluminium oxides (molar proportions MgO-.Al$_2$O$_3$) by precipitation from their salts and calcination. The results are shown in Table III.

TABLE III

| Catalyst | Calcination Temp. °C. | Reaction Temp. °C. | Selectivity of Product | | | | |
|---|---|---|---|---|---|---|---|
| | | | EDC | VC | EC | Other C$_2$-C$_1$ Carbons | CO + CO$_2$ |
| (a) | 300 | 300 | 96.7 | 0.1 | 0.2 | 2.2 | 0.8 |
| | | 350 | 82.2 | 0.5 | — | 11.3 | 6.0 |
| (b) | 400 | 300 | 87.1 | 0.4 | 2.4 | 2.8 | 7.3 |
| | | 350 | 43.2 | 9.7 | 0.1 | 20.9 | 26.1 |
| (c) | 600 | 300 | — | — | 100 | — | — |
| | | 350 | — | — | 100 | — | — |

It was apparent that
(i) catalysts containing as little as 0.9% Cu (0.02 CuO, 0.98 MgO, 1.00 Al$_2$O$_3$) have a similar selectivity for EDC formation at 350° C. as does the conventional catalyst containing 6.5% Cu (as cupric chloride) on alumina;
(ii) that with the catalysts containing MgO there was significantly less burning of ethylene;
(iii) the mixed oxide MgO.Al$_2$O$_3$ did not act as an oxychlorination catalyst.

EXAMPLE 3

Catalysts having the same number of atoms of copper but having different atomic ratios of magnesium to copper were prepared from the appropriate precursors in a manner similar to that of Example 1. The catalysts were of particle size in the range 100 to 350 mesh (British Standard Specification) and were utilised in a fluidised bed. The vol ratio of C$_2$H$_4$:HCl:air was 1:1.9:3 and the gas hourly space velocity was 400 h$^{-1}$. The conditions of the runs and the results obtained are shown in Table IV. The optimum temperature means the temperature at which the HCl conversions are at a maximum and the HCl conversions for runs 1, 2 and 3 were 86%, 90% and 81% respectively. The surface areas of the precursors of Runs 1, 2 and 3 (m$^2$/g) 118, 96 and 84 respectively; the pore volumes (m$^2$/g) were 0.33, 0.38 and 0.38 respectively; their true densities (g/cc) were ca. 3.21 and their apparent densities (g/cc) were 1.6, 1.4, 1.5 respectively.

The conditions of the Runs and the results obtained are shown in Table IV.

TABLE IV

| Run No. | Catalyst (empirical formula) | Calcination temp of catalyst °C. | Catalyst Precursor | Calcination temp of precursor °C. | % Spinel as hereinbefore defined | Optimum Temp °C. | % C$_2$H$_4$ burned at opt temp | % w/w EDC purity |
|---|---|---|---|---|---|---|---|---|
| 1 | CuO 0.08 MgO 0.42 Al$_2$O$_3$ 1.00 | 400 | MgO 0.5 Al$_2$O$_3$ 1.0 | 600 | 13 | 248 | 7.05 | 96.7 |
| 2 | CuO 0.08 MgO 1.92 Al$_2$O$_3$ 1.00 | 400 | MgO 1.0 Al$_2$O$_3$ 1.0 | 600 | 13 | 251 | 1.74 | 98.7 |
| 3 | CuO 0.08 MgO 1.92 Al$_2$O$_3$ 1.00 | 400 | MgO 2.0 Al$_2$O$_3$ 1.0 | 600 | 11 | 257 | 1.30 | 98.9 |

A number of runs were carried out with similarly prepared catalysts each having the 10% by weight copper but having different atomic ratios of magnesium to copper. The conditions of the runs and the results obtained are shown in Table V. The HCl conversions for runs 4, 5, 6 were 97%, 99% and 97%. The EDC purity was ≧99%. The surface areas of the precursors of Runs 4, 5 and 6 (in m$^2$/g) were 118, 107, and 84, respectively; the pore volume (in cc/g) were 0.30, 0.41, and 0.38 respectively; their true densities were (g/cc) ca. 3.1, 3.3, 3.3 and their apparent densities were about 1.6, 1.4 and 1.5 respectively.

TABLE V

| Run No. | Catalyst | Calcination temp of catalyst °C | Catalyst Precursor | Calcination temp of precursor °C | % Spinel as hereinbefore defined | Optimum temp °C | % $C_2H_4$ burned at opt. temp | % $C_2H_4$ burned at 225° C. |
|---|---|---|---|---|---|---|---|---|
| 4 | 0.25 CuO 0.38 MgO 1.00 $Al_2O_3$ | 400 | MgO . $2Al_2O_3$ | 400 | 13 | 225 | 5.13 | 5.1 |
| 5 | 0.25 CuO 0.82 MgO 1.00 $Al_2O_3$ | 400 | MgO . $Al_2O_3$ | 600 | 13 | 238 | 2.86 | 0.8 |
| 6 | 0.33 CuO 1.67 MgO 1.00 $Al_2O_3$ | 400 | 2MgO . $Al_2O_3$ | 600 | 11 | 26 | 4.56 | 0.2 |

Comparison

By way of comparison run 7 was carried out with a conventional catalyst consisting of $CuCl_2$ carried on alumina and containing 10% by weight Cu. The HCl conversion was 98%. The results are shown in Table VI.

TABLE VI

| Run No. | Catalyst | Precursor | Optimum temp °C. | % $C_2H_4$ burned at optimum temp | % $C_2H_4$ burned at 225° C. |
|---|---|---|---|---|---|
| 7 | Conventional | $Al_2O_3$ | 215 | 5.4 | 6.5 |

With the catalysts containing copper, magnesium and aluminium there was no loss by volatilisation nor were there any sticking problems in use. It was apparent that increasing the magnesium content decreased the burning and raised the temperature at which HCl conversion was a maximum. EDC purity was higher at the higher temperatures. A particularly effective catalyst was that having an atomic proportion of one magnesium to two of aluminium.

EXAMPLE 4

Catalyst for use in the process of the invention all containing a high weight % Cu were prepared as follows:

1. This was prepared by co-precipitation at ambient temperature (ca. 20° C.) from the nitrates of magnesium and aluminium by ammonium hydroxide, drying and calcining at 600° C. followed by treatment with copper nitrate solution and calcining at 600° C. as described in Example 1. The catalyst contained 10% Cu, 12.4% Mg, 33.3% Al (corresponding to CuO 0.25, MgO 0.82, $Al_2O_3$ 1.00).
2. This was prepared by impregnating alumina with aqueous magnesium nitrate solution, drying and calcining at 600° C. to give a material of composition MgO.$2Al_2O_3$. The latter was then treated with an aqueous solution of copper nitrate filtered, dried and calcined at 600° C. The catalyst contained 9.3% Cu, 5.2% Mg, 35.8% Al (corresponding to CuO 0.22, MgO 0.32, $Al_2O_3$ 1.00).
3. This was prepared by impregnating alumina with an aqueous solution containing both magnesium and aluminium nitrates, drying and calcining at 600° C. to give a material of composition MgO 0.6, $Al_2O_3$ 1.00). The latter was then treated with an aqueous solution of copper nitrate, dried and calcined at 400° C. The catalyst contained 11.6% Cu, 6.8% Mg, 35.5% Al (corresponding to CuO 0.28, MgO 0.43, $Al_2O_3$ 1.00).

The catalyst was utilised in the oxychlorination of ethylene in a fluidised bed with a $C_2H_4$/HCl/$O_2$ feed in the ratio 1:1.9:3 and a gas hourly space velocity of 400 $hr^{-1}$. The conditions of the run and the results obtained are given are given in Table VII.

TABLE VII

| Catalyst Preparation | Optimum temp for HCl conversion °C. | % $C_2H_4$ burned | % HCl Converted | % w/w Purity of EDC |
|---|---|---|---|---|
| 1 | 238 | 2.86 | 98.8 | 99.0 |
| 2 | 241 | 2.46 | 95.9 | 99.0 |
| 3 | 238 | 5.07 | 99.7 | 99.3 |

Comparison

By way of comparison a run (4) was carried out wherein an alumina was impregnated with an aqueous solution containing copper chloride and magnesium chloride, filtered and dried at 120° C. The catalyst contained 10% by weight Cu and 2.4% by weight Mg. The results are given below:

| Catalyst Preparation | Optimum temp for HCl conversion °C. | % $C_2H_4$ burned | % HCl Converted | % w/w Purity of EDC |
|---|---|---|---|---|
| 4 | 237 | 4.18 | 97.1 | 98.6 |

What we claim is:

1. A method of preparing an oxychlorination catalyst which is an intimate mixture of the oxides of magnesium, aluminum and copper obtained by calcining, wherein the proportion of magnesium oxide is in the range 0.25 to 2.0 moles per mole of aluminum oxide ($Al_2O_3$), said catalyst having a magnesia/alumina spinel structure but not in excess of 40%, said method comprising the steps of precipitating the hydrated oxides of magnesium and aluminum from an aqueous solution of their salts, drying and calcining the hydrated oxides at a temperature in the range 300° C. to 700° C. to form a mixed oxide of magnesium and aluminum, then treating the mixed oxide with a solution of a salt of copper and finally again calcining at a temperature in the range 300° C. to 700° C. to provide the copper oxide.

2. A method of preparing an oxychlorination catalyst which is an intimate mixture of the oxides of magnesium, aluminum and copper obtained by calcining, wherein the proportion of magnesium oxide (MgO) is in the range 0.25 to 2.0 moles per mole of aluminum oxide ($Al_2O_3$), said catalyst having a magnesia/alumina spinel structure but not in excess of 40%, said method comprising treatment of an intimately mixed magnesium oxide/aluminum oxide with an aqueous solution of a copper salt followed by calcination at a temperature in the range 300° C. to 700° C.

3. A method as claimed in claim 1 in which the precipitating agent is an alkali metal hydroxide and in which the precipitate is thoroughly washed.

4. A method as claimed in claim 1 in which the precipitating agent is ammonium hydroxide.

5. A method as claimed in claim 1 in which the calcination temperature is in the range 350° C. to 600° C.

6. A method of preparing an oxychlorination catalyst as claimed in claim 2 in which alumina is mixed with a solution of a magnesium salt decomposable to the oxide, is dried and calcined, and which is then treated with a solution of a copper salt, dried and again calcined.

* * * * *